(12) United States Patent
Maurer et al.

(10) Patent No.: US 9,134,336 B2
(45) Date of Patent: Sep. 15, 2015

(54) DUAL ANALYZER SYSTEM FOR BIOLOGICAL FLUID

(75) Inventors: Elisabeth Maurer, Vancouver (CA); Long Hin Fong, Vancouver (CA)

(73) Assignee: Canadian Blood Services, Ottawa, Ontario (CA)

( * ) Notice: Subject to any disclaimer, the term of this patent is extended or adjusted under 35 U.S.C. 154(b) by 219 days.

(21) Appl. No.: 13/501,282

(22) PCT Filed: Aug. 31, 2010

(86) PCT No.: PCT/CA2010/001365
§ 371 (c)(1),
(2), (4) Date: Apr. 11, 2012

(87) PCT Pub. No.: WO2011/044665
PCT Pub. Date: Apr. 21, 2011

(65) Prior Publication Data
US 2012/0198922 A1    Aug. 9, 2012

Related U.S. Application Data

(60) Provisional application No. 61/252,234, filed on Oct. 16, 2009.

(51) Int. Cl.
*G01N 33/48* (2006.01)
*G01N 35/10* (2006.01)

(52) U.S. Cl.
CPC ................................. *G01N 35/1097* (2013.01)

(58) Field of Classification Search
CPC ......... G01N 21/47; G01N 21/00; B01D 35/00
USPC .............. 356/39, 72, 73, 338; 435/8; 436/94, 436/501; 600/454
See application file for complete search history.

(56) References Cited

U.S. PATENT DOCUMENTS

| | | | |
|---|---|---|---|
| 6,525,807 B1* | 2/2003 | Morikawa et al. | 356/72 |
| 7,472,794 B2* | 1/2009 | Oakey et al. | 210/420 |
| 7,990,525 B2* | 8/2011 | Kanda | 356/73 |
| 2002/0045828 A1* | 4/2002 | Skidmore | 600/454 |
| 2004/0197845 A1* | 10/2004 | Hassibi et al. | 435/8 |
| 2010/0068824 A1* | 3/2010 | Kimura | 436/501 |
| 2010/0225913 A1* | 9/2010 | Trainer | 356/338 |

* cited by examiner

*Primary Examiner* — Tarifur Chowdhury
*Assistant Examiner* — Jamil Ahmed
(74) *Attorney, Agent, or Firm* — Hancock Hughey LLP (57) ABSTRACT

The described apparatus for analyzing a biological sample includes a first analysis instrument fluidly connected to a reservoir for receiving a first flow of the biological fluid and adapted for performing a measurement of a property of the biological sample. A second analysis instrument is fluidly connected to the reservoir for receiving a second flow of the biological fluid and adapted for performing a thermally controlled analysis of the biological sample. The second analysis instrument includes a thermally controlled chamber. A flow stopping device stops the second flow within the thermally controlled chamber in order to allow the second analysis instrument to perform the thermally controlled analysis of the biological sample. The first analysis instrument may include, for example, a hematology analyzer or a flow cytometer, and the second analysis instrument may include, for example, a dynamic light scattering instrument.

18 Claims, 6 Drawing Sheets

DUAL ANALYZER SYSTEM FOR BIOLOGICAL FLUID

CROSS-REFERENCE TO RELATED APPLICATIONS

The present application claims priority on U.S. Provisional Patent Application No. 61/252,234 filed Oct. 16, 2009, the entire content of which is incorporated herein by reference.

TECHNICAL FIELD

The present invention relates generally to biological fluid analyzers.

BACKGROUND

In order to perform a complete analysis of biological fluid such as blood, several analyzers are usually used because a single analyzer may not be capable of conducting the analysis of all of the required blood parameters. A technician in charge of blood analysis has first to insert a blood sample in a first analyzer and perform the first analysis. Subsequently, the technician inserts the blood sample in the second analyzer and performs the second analysis.

This is inconvenient and impractical for a number of reasons. The additional time required to transport the blood sample from the first analyzer to the second analyzer increases the overall analysis time. Further, significant extra costs are involved in having two distinct and separate testing instruments and systems, both in terms of equipment, training, upkeep, etc. Additionally, differing sample requirements for each of the instruments may necessitate that separate samples be prepared, perhaps requiring different preparations times, different sample containers, and the like.

Further, certain instrumentation used to perform analysis on biological samples such as blood require a flow of the fluid through the system (i.e. a flow-through system), while others may require that individual samples of the fluid be extracted from the flow and placed into separate and individual sample containers for testing. Therefore, numerous overlapping steps sometimes need to be performed for the two different analysis instruments, which is ineffective from both a cost and time standpoint.

Therefore, there is a need for an improved method and apparatus for analyzing a biological fluid.

SUMMARY

According to a first aspect of the present invention, there is provided an apparatus for analyzing a biological fluid stored in a reservoir, said apparatus comprising: an analyzer instrument receiving a first flow of the biological fluid, said analyzer instrument adapted for measuring at least one property of said biological fluid; a dynamic light scattering instrument for performing a dynamic light scattering measurement of said biological fluid, said dynamic light scattering instrument including an analysis chamber; a flow splitter in fluid flow communication with both the analyzer instrument and the dynamic light scattering instrument, the flow splitter diverting at least a portion of said first flow towards the analyzer instrument into said analysis chamber of said dynamic light scattering instrument; and a flow stopping device which immobilizes said portion of said first flow within the analysis chamber of the dynamic light scattering instrument, in order to allow said dynamic light scattering instrument to perform said dynamic light scattering measurement of said biological fluid.

In accordance with another aspect of the present invention, there is provided an apparatus for analyzing a biological fluid, said apparatus comprising: a reservoir for receiving said biological fluid; a first analysis instrument being fluidly connected to said reservoir for receiving a first flow of said biological fluid and operable to perform a measurement of a first property of said biological fluid; a second analysis instrument being fluidly connected to said reservoir for receiving a second flow of said biological fluid and operable to perform a thermally controlled analysis of said biological sample, said second analysis instrument comprising a thermally controlled chamber which receives said biological fluid; and a flow stopping device which stops said second flow within said thermally controlled chamber to allow said second analysis instrument to perform said thermally controlled analysis of said biological fluid therein.

In accordance with another aspect of the present invention, there is provided a method for analyzing a biological sample, comprising: propagating a flow of said biological sample from a reservoir toward an analyzer instrument, the analysis instrument measuring at least one property of said biological sample; diverting at least part of said flow into an analysis chamber of a dynamic light scattering (DLS) instrument; stopping said at least part of said flow within said analysis chamber; and measuring a second property of said biological sample within said analysis chamber using said DLS instrument.

In accordance with a further aspect of the present invention, there is provided a method for analyzing a biological sample, comprising: propagating a first flow of said biological sample toward a first analysis instrument adapted to measure a first property of said biological sample; propagating a second flow of said biological sample toward a second analysis instrument, said second analysis instrument being adapted to analyze said biological sample at a controlled temperature; stopping said second flow, thereby obtaining stagnant fluid within said thermally controlled chamber; adjusting a temperature of said stagnant fluid to a target temperature within said thermally controlled chamber; and measuring a property of said stagnant fluid using said second analysis instrument, thereby characterizing a second property of said biological sample.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Figure 1:
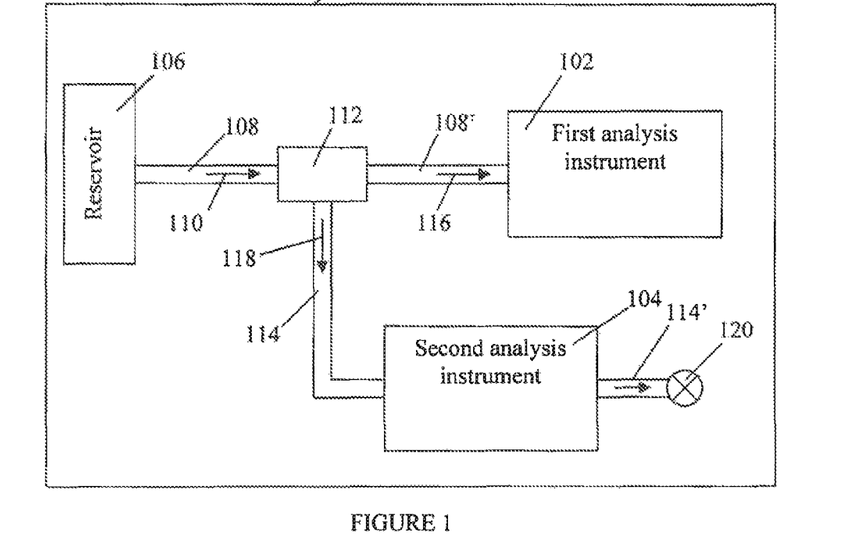
FIG. 1 is a block diagram of an embodiment of the present dual analyzer comprising a first and a second analysis instrument.

Referring to FIG. 1, a biological fluid dual analyzer 100 comprises two interconnected analyzer modules, i.e. a first analysis instrument 102 and a second analysis instrument 104. The dual analyzer 100 includes a reservoir 106 for receiving a biological fluid to be analyzed. The biological fluid being tested and/or analyzed may include, but is certainly not limited to, a blood product such as whole blood, platelet rich plasma, other blood products, urine, synovial fluid, cerebrospinal fluid, tears, and the like.

The reservoir 106 is fluidly connected to the first analysis instrument 102 via first conduits 108 and 108', so that a flow 110 of a sample of the biological fluid may flow or otherwise propagate from the reservoir 106 to the first analysis instrument 102. A flow diverting connection 112, or flow splitter, fluidly connects the first conduit 108 to the fluid conduit 108' and a second conduit 114. The second conduit 114 is fluidly connected to the second analysis instrument 104. The flow diverting connection 112 is adapted to divert at least part of the flow 110 towards the second analysis instrument 104. As a result, the flow 110 propagating from the reservoir 106 is divided into two flows 116 and 118. The first flow 116 of biological fluid propagates from the flow diverting connection 112 towards the first analysis instrument 102 through the conduit 108' and the second flow 118 of biological fluid propagates from the flow diverting connection 112 towards the second analysis instrument 104 via the conduit 114. The propagation of the two split flows 116 and 118 in their respective conduits 108' and 114 can be performed concurrently or successively. The flow diverting connection 112, or flow splitter, therefore allows for at least a part of the flow to the first analysis instrument 102 to be diverted to the second analysis instrument 104, thereby forming parallel flows of the fluid to the two analysis instruments as required.

As will be described further below, in one possible embodiment wherein the biological fluid being analyzed is a blood product, the first analyzer 102 may include a flow cytometer or a hematology analyzer, and the second analysis instrument 104 may include a dynamic light scattering (DLS) instrument.

Referring still to FIG. 1, the dual analyzer 100 also comprises a flow stopping device 120, which in at least one embodiment may be fluidly connected to the second analysis instrument 104, for example via a conduit 114'. The flow stopping device 120, which may comprise a valve for example, is adapted to stop the propagation of the second flow 118 through the conduits 114 and 114' once the flow of biological sample 118 has reached the second analysis instrument 104.

The first analysis instrument 102 which is fluidly connected to the conduit 108' receives the flow 116 and performs a measurement of a first property of the biological sample. The second analysis instrument 104 which is fluidly connected to the conduit 114 receives the flow 118 and measures a second property of the stagnant biological sample contained therein.

The dual analyzer 100 may additionally include a pump connected to the conduit 108 or 108' in order to draw or force the biological sample into the first analysis instrument 102 and to generate the flow 110. The reservoir 106 may contain such a pump, for example a piston pump, adapted to exert a pressure on the biological fluid contained in the reservoir 106 in order to expel the biological fluid through the reservoir outlet conduit 108. Alternately, however, the dual analyzer 100 may include a pump which is operatively connected to the conduit 114 or 114' in order to draw up biological fluid into the conduit 114 from the flow diverting connection 112, and therefore into the second analysis instrument 104.

The reservoir 106 is adapted to directly receive the biological fluid to be analyzed. Alternatively, the reservoir 106 may also be adapted to receive at least one sample holder containing biological fluid to be analyzed.

In one exemplary embodiment, the first analyzer 102 is a flow cytometer or a hematology analyzer and the biological fluid being analyzed is blood. The hematology analyzer 102, for example, may receive the flow of blood (ex: whole blood) and perform an electronic blood cell count such as to determine the composition and concentration of the cellular components of the blood sample. The first analyzer 102 may thus comprise a clinical hematology analyzer, which is automated to determine the presence, number and/or type of cellular elements in collected body fluids, such as blood. The hematology analysis includes determination of non-cellular parameters in blood, such as hemoglobin and hematocrit for example. Hematology analyzers can employ the flow cytometry principle by using hydrodynamic focusing of the sample and measuring static light scattering and fluorescence as well as other techniques such as impedance measurements for example. In a particular embodiment, the hematology analyzer which makes up the first analyzer 102 is an automated high throughput multi-parameter instrument.

Although the first analysis instrument 102 may be a single analysis instrument, such as a hematology analyzer, it may alternately use more than a single technology in order to analyze the biological sample, and may in fact switch between several different possible technologies for analyzing the biological sample. In such a case, the first analysis instrument 102 can be a combination of different analysis instruments.

The hematology analyzer which makes up the first analyzer 102 may be adapted to measure at least one blood property such as red blood counts (RBC), hematocrit (HCT), white blood counts (WBC), mean corpuscular hemoglobin (MCH), mean corpuscular volume (MCV) and mean corpuscular hemoglobin concentration (MCHC). The first analysis instrument can also comprise measurement instruments such as colorimetric analyzer, particle counting means, and the like.

Figure 2:
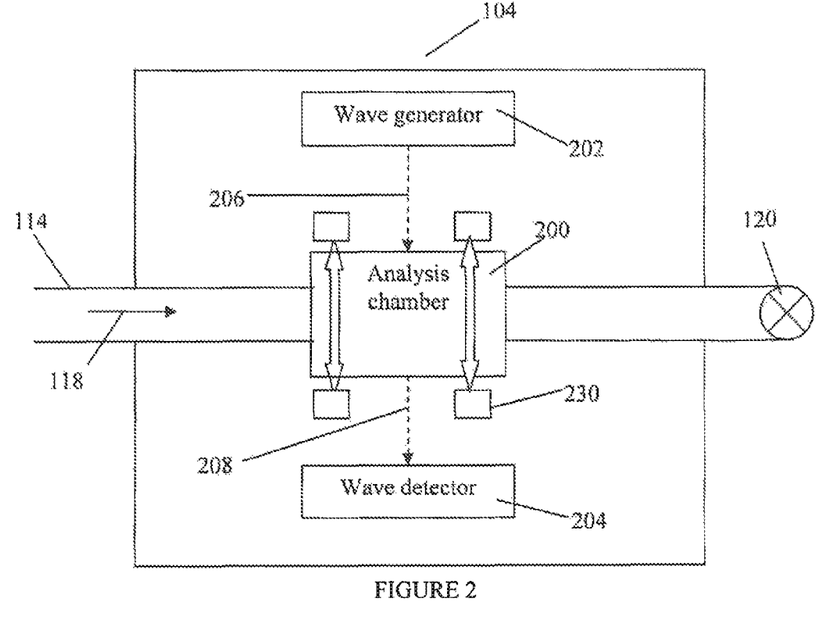
FIG. 2 is a block diagram of the second analysis instrument of FIG. 1.

Referring now to FIG. 2, the second analysis instrument 104 may include a dynamic light scattering (DLS) instrument as described in further detail below. The second analysis instrument 104 in this embodiment therefore includes an analysis chamber 200 adapted to receive the biological fluid to be analyzed. This analysis chamber 200 may be comprised of, for example a capillary which receives the fluid sample therein for testing. At one end, the chamber 200 is connected to the flow diverting connection 112 via the conduit 114 and, at the other end, the chamber 200 is connected to the flow stopping device 120 via the conduit 114'. The second analysis instrument 104 comprises a wave generator 202 and a wave detector 204. The wave generator 202 is adapted to generate waves 206 and to propagate the generated waves 206 into the biological fluid contained in the chamber 200. In order to analyze the biological fluid, the flow stopping device is actuated to stop the flow 118 so that stagnant biological fluid is present in the chamber 200 for the purpose of performing the DLS analysis. Once the diverted sample flow 118 has been detected within the capillary comprising the chamber 200, as described below, and this detected fluid is stationary (i.e. stagnant) within the chamber, the wave generator 202 sends the waves 206 into the chamber 200. The waves 206 interact with the biological fluid in the chamber 220 to give rise to waves 208 which exit the chamber 200. The wave detector 204 is positioned and adapted to measure the waves 208 coming from the chamber 200. The property of the biological fluid to be analyzed by the second analysis instrument 104 is thereby measured using the output waves 208, based on the results of the wave detector 204. Once the measurement is performed, the flow stopping means 120 opens the conduit 114' in order to expel the biological fluid contained in the chamber 200. It should however be understood that the analysis chamber 200 may be made of any adequate material which allows the propagation of the waves 206 and 208 therethrough. For example, at least one part of the chamber 200 may be transparent or translucent to the waves 206 and 208.

The DLS system of the second analysis instrument 104 may also be able to detect whether the chamber 200 actually contains the fluid therein, such as to confirm that the DLS measurement can begin. For example, in one particular embodiment, the DLS system of the second analysis instrument includes a fluid detection system having at least one detector 230 (see FIG. 2), although in the embodiment depicted in FIG. 2, two such detectors 230 are disposed on either side or end of the chamber 200 (composed for example of a capillary) such as to be able to detect a change in light transmission for a predetermined period of time, for example a minimum period of time of 2 seconds. Once this change in light transmission has been detected for at least 2 seconds, thereby confirming that the chamber now contains fluid therein, the system then permits the DLS measurements to begin on the fluid within the chamber 200. The detectors 230 on either side of the analysis chamber 200 may be any suitable type of detectors capable of determining whether or not any fluid is present within the chamber. In a particular embodiment light detectors were used, as they are non-invasive, relatively inexpensive and straightforward to use and operate. The use of the detectors 230 has been found to be particular important and useful. This is due to the fact that the first analysis instrument 102, for example the flow cytometer or hematology analyzer, does not require the detection and determination that sufficient fluid is present for analysis because these instruments are flow-through type devices which measure "snap shots" of particles flowing therethrough. If no fluid sample was present within the flow cytometer or hematology analyzer of the first analysis instrument 102, it would likely simply take longer to accumulate the information required to perform its analysis. However, the DLS measurement system of the second analysis instrument 104 is a technique which accumulates data over a set period of time from a relatively small sample observation volume in the chamber 200 (ex: a capillary). Therefore, before any DLS measurements can be taken on the chamber 200, it has been found important to first make sure that this volume (the chamber 200) contains the sample to be tested. The detectors 230 permit this, and also therefore serve as a double-check that the flow diverting device is working as required. While FIG. 2 illustrates a second analysis instrument 104 in which the wave generator 202 and the wave detector 204 are positioned on opposite sides of the chamber 200 in order to perform a wave transmission measurement of the biological fluid, it should be understood that the wave generator 202 and the wave detector 204 may be positioned on the same side of the chamber 200 in order to perform a wave reflection measurement (such as by measuring the dynamic light scattering) of the biological fluid. It should also be understood that more than one wave detector 204 can be used detect the waves 208, each positioned at a corresponding angle relative to the generated waves 206 in order to collect waves scattered from within the chamber 200. It should also be understood that at least one waveguide connected to a wave detector can be positioned in the vicinity of the chamber 200 in order to collect the waves 208 and guide the waves 208 up to the detector.

Further, the flow stopping device 120 may be any adequate device capable of preventing flow of the fluid in and/or through the analysis chamber 200, such as a device capable of temporarily obstructing the conduit 114'. For example, the flow stopping device 120 can comprise a valve adapted to open and close the conduit 114'. In an embodiment where the dual analyzer 100 comprises a pump adapted to draw the biological fluid into the chamber 200 from the flow diverting connection 112, the pump may act as the flow stopping device 120. For example, the pump may be positioned at the end of the conduit 114' opposite to the analysis chamber 200. When the pump is operated, biological fluid (ex: blood) is drawn up into the conduit 114 from the flow diverting connection 112 to give rise to the flow 118. When the pump stops operating, the flow 118 stops flowing through the conduits 118 and 118', and stagnant biological fluid is present within at least the chamber 200.

The wave generator 202 may emit any adequate waves adapted to measure a property of a biological fluid. For example, the wave generator may be adapted to emit microwaves, near infrared light, and the like. The wave detector 204 is adapted to detect and measure properties of the wave generated by the wave generator 202.

Figure 3A:
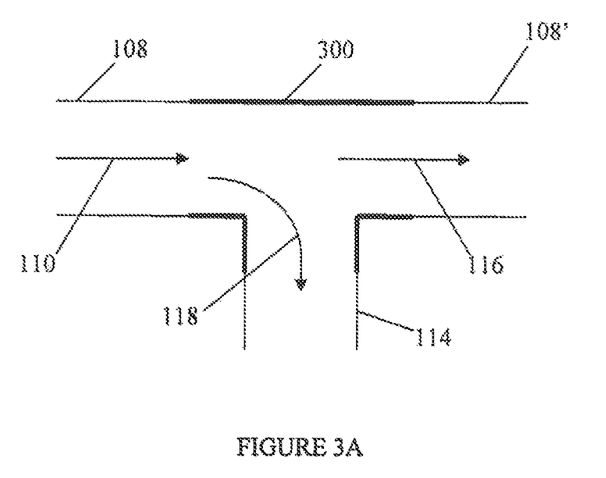
FIG. 3A is a schematic cross-sectional view of an embodiment of a flow diverting connection including a T-shaped connector.

Referring now to FIG. 3A, a flow diverting connection 112 in accordance with one possible embodiment is depicted and includes a T-shaped connector 300. The connector 300 comprises one input connected to the conduit 108 and two outputs connected to the conduits 108' and 114. The flow of biological fluid 110 propagating in the conduit 108 is thereby divided into the flows 116 and 118 by the T-shaped connector 300. When the flow stopping device 120 is actuated, biological fluid accumulates within the conduits 114 and 114' and the chamber 200, while the main flow 116 continues flowing through the conduit 108' to the first analysis instrument 102. Once the conduits 114 and 114' and the chamber 200 are filled with biological fluid, the flow 118 stops propagating and substantially the entirety of the flow 110 propagates into the conduit 108'.

Figure 3B:
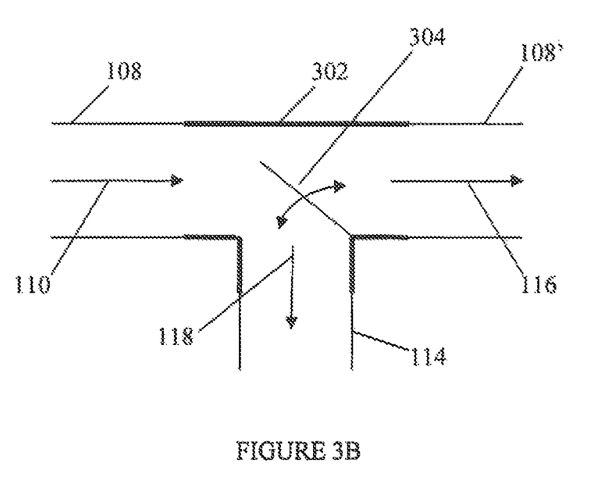
FIG. 3B is a schematic cross-sectional view of an alternate embodiment of a flow diverting connection, including a valve system.

FIG. 3B illustrates another embodiment of a flow diverting connection 112 comprising a T-shaped connector 302 and a valve 304. The T-shaped connector 302 divides the flow 110 into flows 116 and 118. The valve 304 is adapted to regulate the flows 116 and 118. For example, the valve 304 may partially obstruct the conduits 108' and 114 so that the flows 116 and 118 propagate into their respective conduit 108' and 114. The valve 304 may substantially hermetically obstruct the conduit 108' or 114, so that only the flow 118 or 116, respectively, propagates into its respective conduit 114, 108'.

Such a connector 302, having a valve 304, allows the measurements of the biological fluid performed by the first and second analysis instruments 102, 104 to be performed concurrently or sequentially.

While the present description refers to T-shaped connectors, it should be understood that other connectors having any other shapes may also be used, such as Y-shaped connectors for example. It should also be understood that any adequate flow regulating device may be used, such as flow diverting valves, etc. In all cases, however, the flow regulating device is capable of diverting either part or all of the main fluid flow 110 towards the second analysis instrument 104, and this in either a continuous or periodic fashion (i.e. at predetermined, but not necessary regular, intervals). Any valves or combination of valves may be used to regulate the flows 118 and 116 propagating into the conduits 108' and 114, respectively. For example, a ball valve, an L-shaped 3-way valve, a T-shaped 3-way valve, a controlled flow valve such as a plug valve, or the like may be used. In another example, a tap or faucet may be used to regulate the flows 116 and 114. In one embodiment, the regulation of the flows 116 and 114 is performed independently one from the other.

In a particular embodiment of the present system, the analysis chamber 200 is in thermal connection with a heating and/or cooling device in order to heat and/or cool the biological fluid contained in the chamber 200 to maintain the fluid at a target temperature. Any heating and or cooling device may be used. For example, a Peltier heating/cooling device, a thermo-electric heating/cooling device, or the like can be used. It should be understood that the heating and/or cooling device may be integral with the chamber 200, or alternately may be disposed on either or both ends thereof at an inlet and/or an outlet. Using the heating and/or cooling device, the biological fluid can experience a temperature cycle to obtain functional information about the biological fluid.

The above-mentioned pump propagates the flow of biological fluid 110 from the reservoir 106 into the conduit 108. When reaching the flow diverting connection 112, at least part of the flow 110 is diverted into the conduit 114 to give rise to the flow 114. When the analysis chamber 200 of the second analysis instrument 104 is filled with biological fluid, the flow stopping device 120 is actuated to stop the flow 114 propagating, thereby obtaining substantially stagnant biological fluid into the chamber 200. The stagnant biological fluid is heated or cooled to reach a target temperature, and waves are emitted and propagated into the stagnant biological fluid and subsequently collected in order to measure a property of the biological fluid. It should be understood that the temperature of the stagnant biological fluid may be adjusted during the measurement of the property. For example, the temperature of the stagnant biological sample may experience a temperature cycle during the analysis of the biological fluid.

Figure 4:
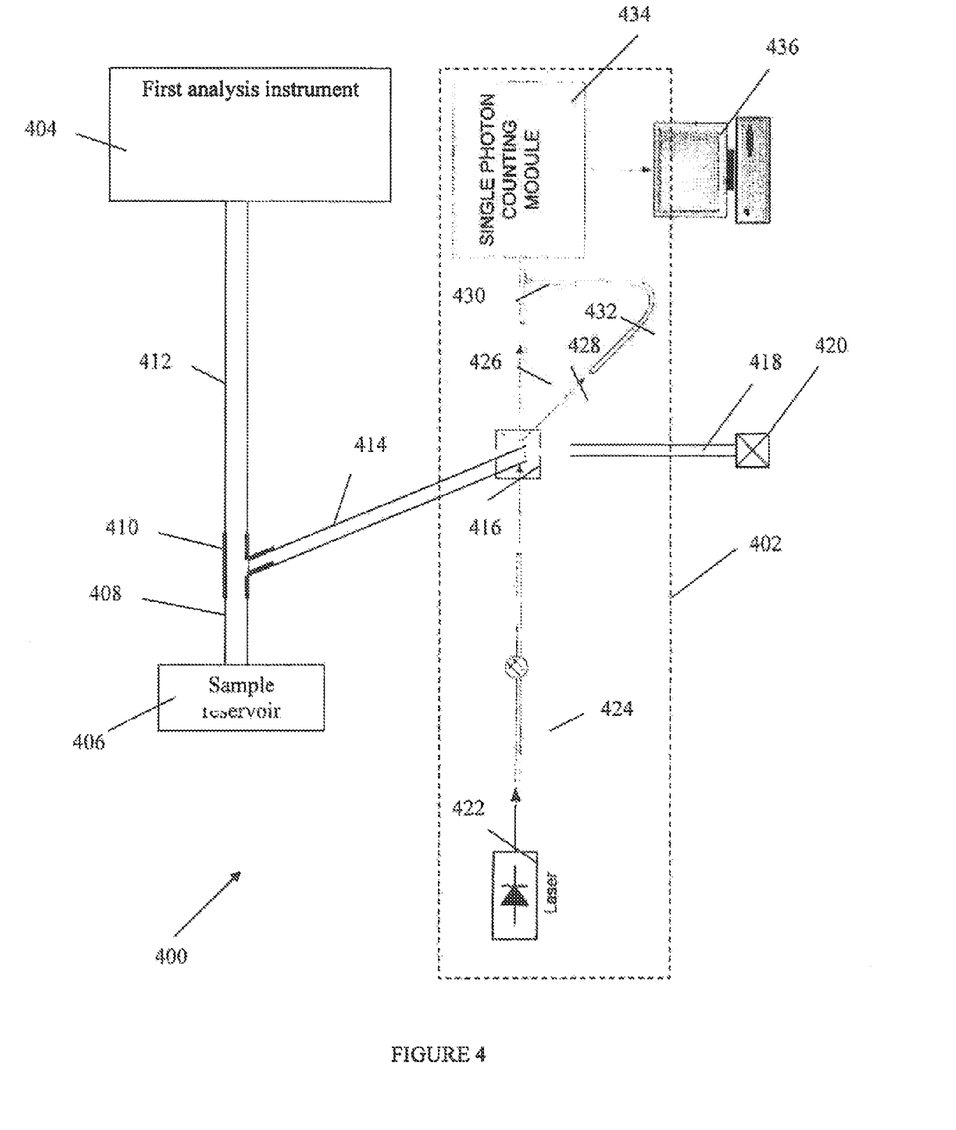
FIG. 4 is a block diagram of a dual analyzer comprising a dynamic light scattering instrument.

Referring now to the embodiment of FIG. 4, a dual analyzer 400 in which the second analyzer 402 is a dynamic light scattering (DLS) instrument adapted to determine the size distribution profile of platelets, small particles and/or microparticles in a biological fluid such as whole blood, a platelet rich plasma, or other blood products, for example. The dual analyzer 400 comprises a first analysis instrument 404 fluidly connected to a sample reservoir 406 adapted to receive a biological fluid to be analyzed. The fluidic connection between the first analysis instrument 404 and the reservoir 406 comprises two conduits 408 and 412, and a flow diverting connection 410. One end of the conduits 408 and 412 is fluidly connected to the flow diverting connection 410 while the other end is fluidly connected to the sample reservoir 406 and the first analysis instrument 414, respectively. A pump (not shown) draws a flow of the biological fluid (ex: blood) from the reservoir 406 into the conduit 408 towards the first analysis instrument 404. At least part of the flow of biological fluid is diverted by the flow diverting connection 410 into a conduit 414 fluidly connected to an analysis chamber 416 of the DLS instrument 402. The analysis chamber 416 is also fluidly connected to a conduit 418 at the end of which a pump 420 acts as a flow stopping device.

The flow diverting connection 410 is provided with a valve adapted to substantially hermetically close the conduit 414 when an adequate amount of biological fluid has entered into the conduit 414. Such an "adequate" amount of biological fluid may include, for example, when the capillary which makes up the analysis chamber 416 is filled. This can be indicated by positive feedback from the above-mentioned light detectors on either side of the capillary, such as to indicate that the capillary chamber 416 is filled with the biological fluid. Once such positive feedback has been received by the system for at least 2 seconds, thereby ensuring proper filling of the chamber, the DLS measurements of the fluid within the chamber can then begin. The pump 420 therefore draws up the adequate amount of biological fluid into the analysis chamber 416 and stops operating. Once the biological fluid contained in the analysis chamber 416 is stagnant, a DLS measurement of the biological fluid can be performed by the DLS instrument 402. The pump 420 may also be used to expel the biological fluid from the analysis chamber 416 once the DLS measurement has been performed.

The DLS instrument 402 comprises a light source such as, for example, a laser diode 422 which is powered by a power supply. The laser diode 422 generates and emits a beam of laser light into a length of optical fiber 424. In one embodiment, the laser generates light at 635 nm, for example, although any other adequate wavelengths could be used, as would be appreciated by those of ordinary skill in the art. As is also known in the art, the intensity of the laser beam can be adjusted using an adjustable neutral density filter (or by using an attenuator in the fiber) which allows the laser to be operated at maximum power while curtailing the intensity of the incident light. This reduces multiple scattering and other undesirable optical effects that can arise when the intensity of the incident light is too high. The optical fiber 424 is preferably a single-mode, polarization-maintaining optical fiber which, as is well known in the art, prevents the polarization from drifting when the light propagates through the optical fiber or, alternatively, a multimode fiber can be utilized. As is known in optics, polarization-maintaining fibers can be made using fibers of noncircular cross-section or by making the propagation medium of the fibers anisotropic such as, for example, by stressing the fibers in a specific direction. The polarized laser light emerges from the single-mode, polarization-maintaining optical fiber 424 and travels a short distance through the air before reaching the analysis chamber 416. This incident light impinges on the biological fluid contained within the analysis chamber 416.

The incident light scatters when photons strike the particles suspended in the biological fluid within the analysis chamber 416. The scattered light 426, 428 scatters in various directions away from the biological fluid. A portion of this scattered light is collected by light collectors 430, 432, which can be optical fibers connected to a single-photon counting module 434 powered by a power supply. The single-photon counting module 434 transmits the measured data to a processing unit 436 which can be external or internal to the dual analyzer 400.

The single-photon counting module 434 may generate TTL pulses (transistor-transistor logic pulses) and transmits the generated TTL pulses to a data acquisition card comprised into the processing unit 436. The data acquisition card digitizes the TTL pulses and communicates the "raw data" to a processor of the processing unit 436. Alternatively, a hardware correlator such as a multi-tau correlator can be used instead of the data acquisition card. In this case, the hardware correlator generates and transmits a correlation function to the processing unit 436.

At least one heating and/or cooling element may also be provided, and is disposed in heat transfer communication with the analysis chamber 416, in order to control and/or adjust the temperature of the biological sample within the analysis chamber 416 of the DLS instrument. This may include, for example, heating and cooling the sample using the heating and/or cooling element in order to maintain the sample at a target temperature.

The processing unit 436 is adapted to determine the size or hydrodynamic radius of the microparticles within the biological fluid by correlating the observed speckle pattern that arises due to Brownian motion and solving the Stokes-Einstein equation, which relates the particle size to the measured diffusion constant.

Figure 5:
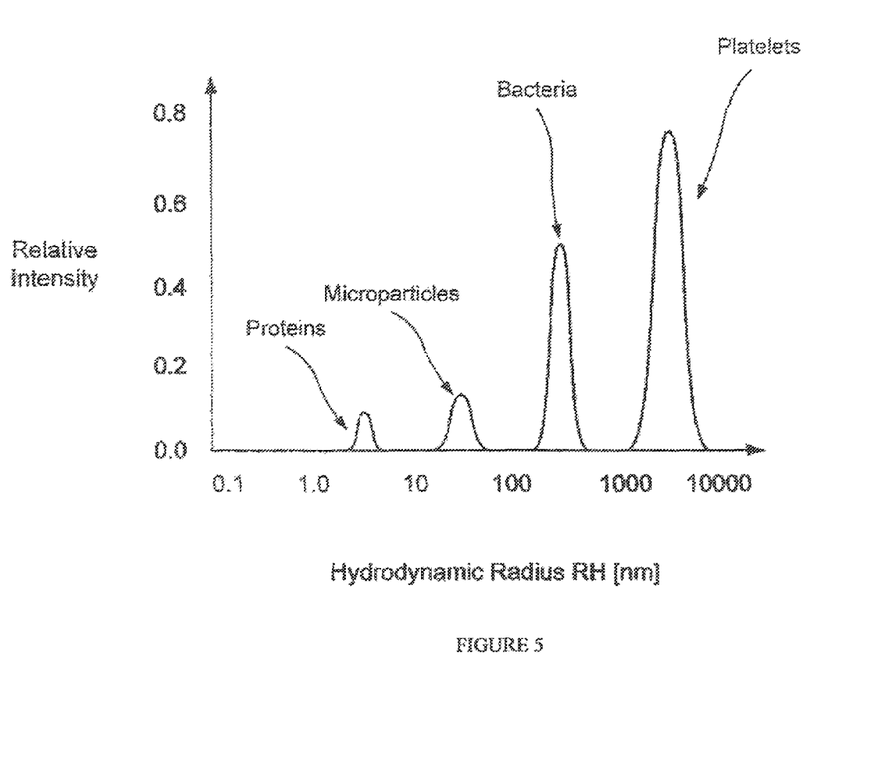
FIG. 5 is a particle size distribution plot.

The processing unit 436 generates a correlation function and then generates a size distribution plot, for example as illustrated in FIG. 5, which is displayed on a display unit to a researcher, clinician, or other end-user. Alternatively, size distribution data can be presented in tabular form or in any other intelligible manner, such as for example by a summarizing single parameter. This single parameter can include a DLS score, for example.

The size distribution plot may show a representative distribution of hydrodynamic radii for platelets, bacteria, microparticles and proteins detected within a biological fluid, as measured by the DLS instrument 402. The size of individual microparticles and/or the average size of all microparticles detected using the DLS measurements can be determined. The hydrodynamic radii are calculated from the DLS "speckle pattern", as is known in the art. The size distribution plot readily enables researchers, technicians, clinicians or other end-users to detect the presence and level of microparticles in the biological fluid, for example of a whole blood or platelet rich plasma.

In a particular embodiment of the dual analyzer system, the processing unit 436 also generates and outputs the measured data, i.e. the level and make up of microparticles in the tested fluid sample. This data generated by the processing unit 436 may include the quantitation of microparticles, as well as whether the quantity of microparticles exceeds a predetermined maximum threshold or falls below a predetermined minimum threshold, for example. In the same or an alternate embodiment, the processing unit 436 can be adapted to attempt to identify the size and/or type of measured microparticles by comparing a measured hydrodynamic radius of the microparticles to previously obtained data and/or other empirical data, stored into a memory of the processing unit 436. The processing unit 436 may also be adapted to provide an indication to the user, such as a visual or audible warning, which indicates that the measured quantity of microparticles falls outside the predetermined or expected normal envelope, for example.

The DLS instrument 402 of the dual analyzer 400 is adapted for diagnosing an existing medical condition or a possible medical condition by detecting microparticles in blood or other bodily fluids using dynamic light scattering. When the reservoir 406 receives whole blood, a filter may be positioned along the conduit between the flow diverting connection and the chamber of the DLS instrument in order to remove large blood cells, such as red blood cells or white blood cells, and therefore prevent the propagation of whole blood so the level of microparticles within the remaining platelet rich plasma can be measured by the DLS instrument 402. By filtering the flow directed to the analysis chamber of the DLS instrument, thus removing the large blood cells using a filter, it is possible to obtain platelet rich plasma. Any suitable device adapted to remove large blood cells from blood can be used as a filter. For example, the filter adapted to prevent large cells from propagating may be positioned between the flow diverting connection and the analysis chamber of the second analysis instrument (i.e. upstream of the analysis chamber). The filter can be a net or mesh-type filter provided with holes or pores having an adequate dimension, for example. Particles having a dimension inferior to that of the holes can pass trough the filter while particles having a dimension substantially equal or superior to that of the holes are stopped and prevented from propagating. As the biological fluid propagates through the filter, holes of the filter are blocked by the particles having a dimension at least equal to that of the holes. In a particular embodiment, a removable filter is provided upstream from the analysis chamber for filtering said at least part of the flow diverted towards the DLS instrument. This filter may be readily accessible such that it can be replaced prior to performing DLS measurements on each new biological sample. Accordingly, each sample is thereby filtered with a new filter, and therefore the filter needs to be easily changeable, such as by using a Luer-type fitting between both the filter bottom and the incoming fluid conduit tubing, and between the filter top and the outgoing fluid conduit tubing. This configuration of the filter ensures a convenient access such as to replace the filter on a sample-by-sample basis.

In an alternate embodiment, the filter itself may act as the flow stopping device. In this case, the filter is sized and shaped such that substantially all of the holes of the filter are blocked after a predetermined volume of biological fluid has propagated through the filter. As a result, the propagation of the biological fluid is stopped by the filter itself after a predetermined quantity of the fluid has been filtered.

The DLS instrument 402 may be adapted to identify optical characteristics of either the detected microparticles or immunological markers such as fluorescently labeled antibodies or other light emitting chemicals which bind to certain microparticles. It is of note that the term "microparticles" as used herein is understood to mean particles within bodily fluids (such as blood), which have a hydrodynamic radius of less than about 1 micron. For example, the term "microparticles" may refer to particles having a hydrodynamic radius of between about 20 and about 1000 nm. In another example, the term "microparticles" may refer to particles having a hydrodynamic radius of between about 50 nm and about 499 nm. In the same or an alternate embodiment, the term "microparticles" is also intended to include so-called "nano-particles".

The dual analyzer of the present disclosure is therefore adapted to analyze at least two properties of any biological fluid and colloids. Examples of biological fluids are whole blood, platelet rich plasma, other blood products, urine, synovial fluid, cerebrospinal fluid, tears, and the like.

In one embodiment, the dual analyzer 100 is adapted to be connected to an external processing unit. The external processing unit is adapted to receive data representative of the measurements performed by the first and second analysis instruments 102 and 104. The external processing unit may also be adapted to process the received data in order to generate information of interest about the measured properties.

In another embodiment, the dual analyzer 100 comprises a memory and an internal processing unit which is in communication with the first and/or second analysis instruments 102 and 104. The internal processing unit is adapted to process data representative of the measurements performed by the first and/or second analysis instruments 102 and 104 and to generate information of interest about the measured properties. The dual analyzer may also comprise a display in order to display the information of interest to a user and/or a printer to print the information of interest. Alternatively, the display and/or the printer may be external to the dual analyzer 100.

Referring back to FIGS. 1 and 2, the dual analyzer 100 comprises a control unit connected to the flow diverting connection 112 and/or the flow stopping device 120 and adapted to control the flow diverting connection 112 and/or the flow stopping device 120. In this case, the flows 118 and/or 116 are regulated by the control unit. The control unit may also be adapted to perform the analysis of the measurements performed in the first and/or second analysis instruments. In this case, the control unit comprises a memory and a processor adapted to receive and process data representative of the measurements performed by the first and/or second analysis instruments 102 and 104 and to generate information of interest about the measured properties.

The conduits of the dual analyzer may also be fluidly connected to a reservoir of cleaning solution. When the conduits of the dual analyzer and the analysis chamber of the second analysis instrument need to be cleaned, a pump propagates the cleaning solution into the conduits and the chamber. It should be understood that any adequate cleaning solution can be used. A filter may be positioned along the conduit connecting the reservoir to the flow diverting connection, the conduit connecting the flow diverting connection to the first analysis instrument, and/or the conduit connecting the flow diverting connection to the second analysis instrument. In an embodiment where the biological fluid to be analyzed is blood, a filter adapted to remove red cells and/or white cells is positioned along the conduit connecting the analysis chamber of the second analysis instrument to the flow diverting connection.

While the present description refers to a second analysis instrument comprising a DLS instrument, it should be understood that the second analysis instrument may comprise an alternate medical analysis instrument, such as an alternate optical analysis instrument adapted to measure the Doppler shift of a wave.

Figure 6:
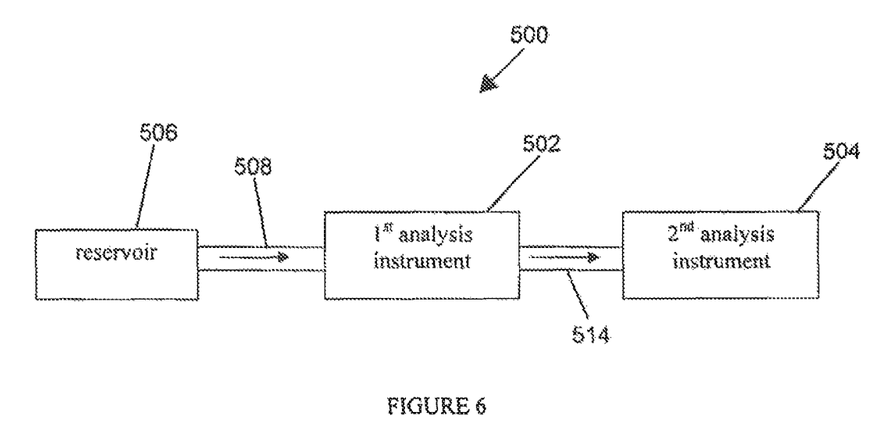
FIG. 6 is a schematic flow diagram of a dual-analyzer in accordance with an alternate embodiment.
Figure 7:
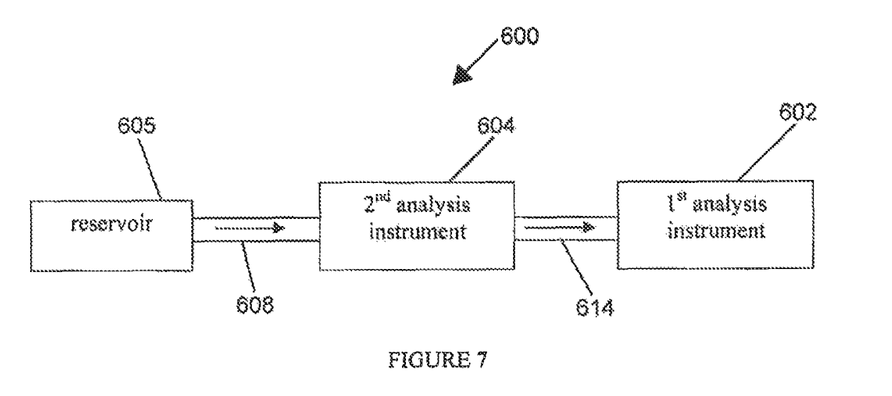
FIG. 7 is a schematic flow diagram of a dual-analyzer in accordance with another alternate embodiment.

While FIGS. 1 and 4 illustrate dual analyzers 100, 400 in which a first and a second analysis instruments are connected in parallel with respect to a reservoir, it should be understood that the first and second analysis instruments can also be connected in series, as illustrated in FIGS. 6 and 7 for example.

In the embodiment shown in FIG. 6, the dual analyzer 500 includes a first analysis instrument 502 that is fluidly connected to the reservoir 506 by a conduit 508 and the second analysis instrument 504 is fluidly connected to the first analysis instrument 502 by another conduit 514. A flow of biological fluid therefore propagates from the reservoir 506 to the first analysis instrument 502, wherein a first analysis of the biological fluid is performed while the biological fluid is within the first analysis instrument. Then, the biological fluid flows directly from the first analysis instrument 502 to the second analysis instrument 504, which is fluidly connected in series therewith. In order to perform a thermally controlled analysis of the biological fluid, a flow stopping device may be actuated to stop the flow of the biological fluid within the analysis chamber of the second analysis instrument 504, so that stagnant biological fluid is present into the analysis chamber for at least a given period of time required for obtaining test measurements (ex: DLS measurements).

In the embodiment illustrated in FIG. 7, the dual analyzer 600 includes a second analysis instrument 604 that is fluidly connected to the reservoir 605 by a conduit 608 and the first analysis instrument 602 is directly fluidly connected to the second analysis instrument 604 by another conduit 614. A flow of biological fluid therefore propagates from the reservoir 605 directly to the second analysis instrument 604. In order to perform a thermally controlled analysis of the biological fluid, a flow stopping device is actuated to stop the flow of the biological fluid in an analysis chamber of the second analysis instrument 604 so that stagnant biological fluid is present in the analysis chamber. Once the thermally controlled analysis is completed within the second analysis instrument 604, the biological fluid is then sent from the second analysis instrument 604 to the first analysis instrument 602, within which another analysis is performed on the same sample of the biological fluid.

While FIGS. 1 and 4 illustrate dual analyzers 100, 400 in which the second analysis instrument is fluidly connected to a conduit connecting the first analysis instrument to a reservoir via a flow diverting connection, it should also be understood that the second analysis instrument may be directly connected to the reservoir via another conduit.

Figures 8, 8A, 8B:
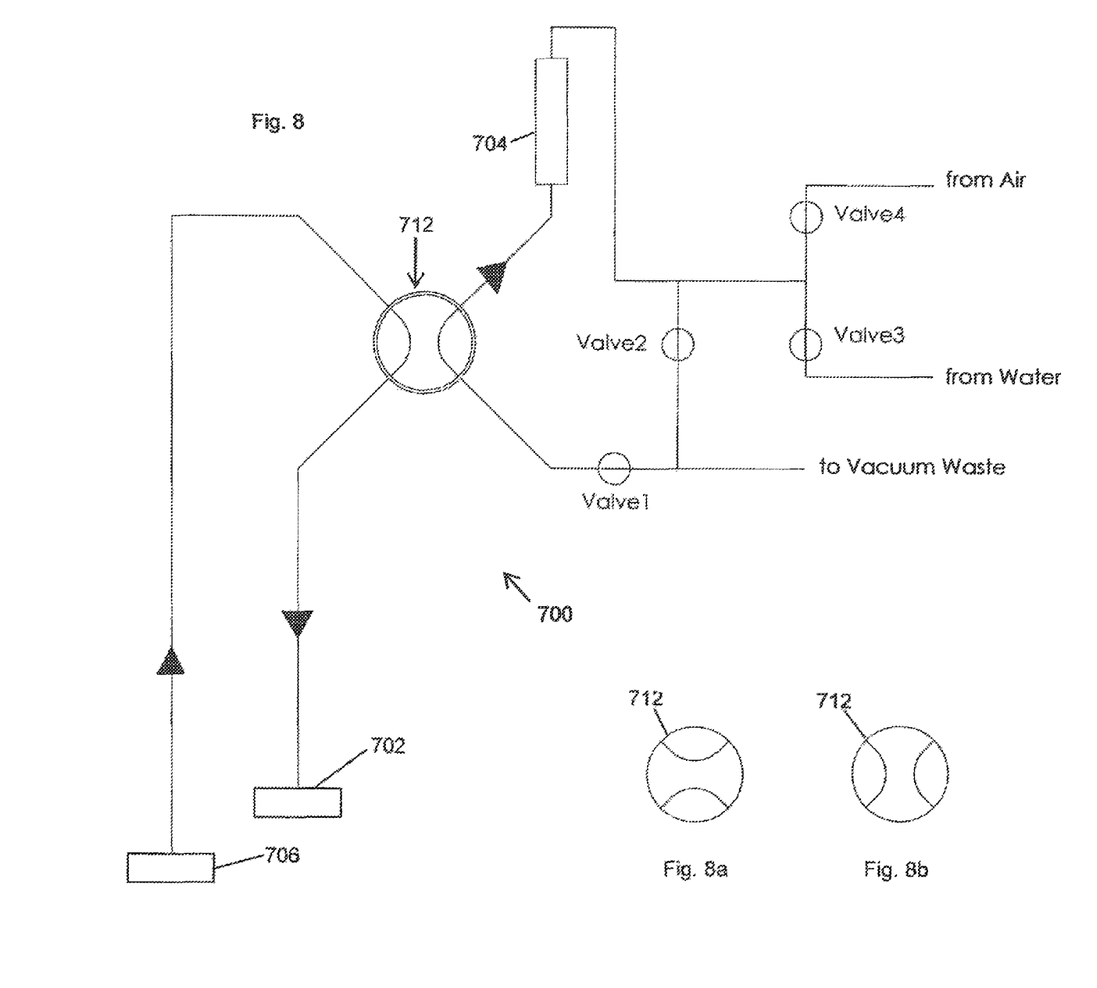
FIG. 8 is a schematic flow diagram of a further embodiment of the present dual-analyzer system, having a four-way valve as a flow diverting connection.
FIG. 8A is a schematic plan view of the four-way valve of FIG. 8, shown in a position wherein all flow is diverted to the DLS instrument of the second analysis instrument.
FIG. 8B is a schematic plan view of the four-way valve of FIG. 8, shown in a position wherein all flow is diverted to the flow cytometer or a hematology analyzer of the first analysis instrument.

Referring now to FIG. 8, a schematic flow diagram of a dual-analyzer 700 of a further embodiment is depicted, wherein fluid flow from common fluid sample source, such as a sample reservoir 706, before being split into parallel flows and/or directed into either one or both of two different flow paths (one for each of the first analysis instrument 702 and the second analysis instrument 704) before the flows converge again into one waste exit. As per the dual analyzer 100 described above, which includes a flow diverting connection 112, the dual analyzer 700 of the present embodiment includes a flow diverting connection, or flow splitter, 712, which serves to divert either all or only a portion of the flow to one or both of the analysis instruments. Therefore, the flow diverting connection 712 can direct all flow to a single one of the first and second analysis instruments, or can also permit the inlet flow to be split into two concurrent and parallel flows, one flowing to each of the two analysis instruments, which both originate from a common fluid sample. In this manner, both instruments can be provided with flow simultaneously, or alternately only one or the other of the two instruments can be fed the entire inlet fluid flow. The flow diverting connection 712 includes, in at least this embodiment, a four-way valve. The four-way valve 712 allows the flow of the biological fluid sample from the common sample source, i.e. the reservoir 706, to be split and directed to both analysis instruments 702 and 704 in parallel, or alternately can direct all of the input flow from the reservoir 706 to only one of the two instruments 702, 704. As per the embodiment described above, the first instrument 702 may include a flow cytometer or a hematology analyzer and the second analysis instrument 704 may include a dynamic light scattering (DLS) instrument. By controlling the four-way valve 712, the flow of sample fluid can be varied and controlled as desired, in order to direct as much or a little fluid sample to either, or both, of the first and second analysis instruments 702, 704. As seen in the flow diagram of FIG. 8, common water and air inputs to the dual analyzer 700 may also provided regardless of which position the four-way valve 712 is in, and a single outlet to vacuum waste is also provided. A number of additional valves in the flow system are used to direct the input and waste output flows as required, depending on the position of the valve 712 and the input flow to one or both of the first and second analysis instruments 702, 704.

FIG. 8A shows a position of the four-way valve 712 wherein all of the inlet from the reservoir 706 is directed exclusively to the DLS instrument of the second analysis instrument 704. FIG. 8B shows a position of the four-way valve 712 wherein all flow is diverted exclusively to the flow cytometer or a hematology analyzer of the first analysis instrument 702. It is to be understood that partial opening of the valve 712 is also possible, such that the inlet flow from the reservoir can be split, in any ratio, between the first and second analysis instruments 702,704, thereby providing two parallel flows downstream of the four-way valve 712 which simultaneously feed both the first analysis instrument 702 (ex: flow cytometer or a hematology analyzer) and the second analysis instrument 704 (ex: DLS measurement instrument).

The embodiments of the present disclosure described above are intended to be examples only. Those of skill in the art may effect alterations, modifications and variations to the particular example embodiments without departing from the intended scope of the present disclosure. In particular, selected features from one or more of the above-described example embodiments may be combined to create alternative example embodiments not explicitly described, features suitable for such combinations being readily apparent to persons skilled in the art. The subject matter described herein in the recited claims intends to cover and embrace all suitable changes in technology.

The invention claimed is:

1. An apparatus for analyzing a biological fluid, said apparatus comprising:
 a flow path for delivering a flow of the biological fluid to a first analyzer instrument and, separately, to a dynamic light scattering instrument having an analysis chamber adapted for retaining a volume of biological fluid containing platelets, small particles and/or microparticles;
 a flow splitter in the flow path, the flow splitter diverting at least a portion of said flow to said analyzer instrument and at least a portion of said flow to the analysis chamber of said dynamic light scattering instrument;
 said first analyzer instrument adapted for measuring at least one property of said biological fluid;
 said dynamic light scattering instrument adapted for performing a dynamic light scattering measurement of said biological fluid in the analysis chamber;
 a fluid detection system operable to detect when the analysis chamber comprises the biological fluid in said chamber over a predetermined minimum period of time; and
 a flow stopping device which immobilizes said portion of said flow within the analysis chamber of the dynamic light scattering instrument, in order to allow said dynamic light scattering instrument to perform said dynamic light scattering measurement of said biological fluid once said fluid detection system has detected said biological fluid in said chamber for said predetermined minimum period of time, without immobilizing said portion of said flow to said analyzer instrument.

2. The apparatus of claim 1 wherein said analyzer instrument comprises one of a hematology analyzer and a flow cytometer.

3. The apparatus of claim 2 wherein the dynamic light scattering instrument includes a temperature controller in thermal communication with the analysis chamber to control a temperature of said biological fluid within the analysis chamber.

4. The apparatus of claim 3 further comprising a control unit operatively connected to said flow stopping device and adapted to control said flow stopping device.

5. The apparatus of claim 4 further comprising a control unit operatively connected to said flow splitter for controlling said flow splitter.

6. The apparatus of claim 5 further comprising a cell filter positioned between said flow splitter and said analysis chamber.

7. The apparatus of claim 1 further comprising said fluid detection system including one or more light detectors disposed proximate the analysis chamber, the light detectors determining a change in light transmission through the analysis chamber over predetermined minimum period of time to confirm that the analysis chamber contains the biological fluid.

8. The apparatus of claim 7, wherein the dynamic light scattering instrument initiates the dynamic light scattering measurement once said change in light transmission is detected by the fluid detection system for said predetermined minimum period of time.

9. An apparatus for analyzing a biological fluid, said apparatus comprising:
 a reservoir for receiving said biological fluid, said reservoir defining a flow path from said reservoir;
 a flow splitter in the flow path, said flow splitter splitting a flow of said biological fluid from said reservoir into a first flow in a first flow path and a second flow in a second flow path;
 a first analysis instrument being fluidly connected to said reservoir for receiving a first flow path of said biological fluid and operable to perform a measurement of a first property of said biological fluid as said first flow of said biological fluid flows through said first analysis instrument;
 a second analysis instrument being fluidly connected to said second flow path of said biological fluid and operable to perform a thermally controlled analysis of said biological sample, said second analysis instrument comprising a thermally controlled chamber which receives said biological fluid;
 a fluid sensor for detecting when fluid is in the chamber; and
 a flow stopping device which (a) stops said second flow within said thermally controlled chamber to allow said second analysis instrument to perform said thermally controlled analysis of stagnant biological fluid therein and (b) does not stop said first flow of said biological fluid through said first analysis instrument.

10. The apparatus of claim 9 further comprising a flow diverting connection for diverting at least part of said first flow into said thermally controlled chamber of said second analysis instrument, said at least part of said first flow corresponding to said second flow.

11. The apparatus of claim 10 wherein said first analysis instrument comprises a hematology analyzer.

12. The apparatus of claim 11 wherein said hematology analyzer comprises a flow cytometer.

13. The apparatus of claim 12 wherein said second analysis instrument comprises a thermally controlled analysis instrument adapted to measure a wave Doppler shift.

14. The apparatus of claim 13 wherein said thermally controlled analysis instrument comprises a dynamic light scattering instrument.

15. A method for analyzing a biological fluid, said method comprising:
 propagating a flow of biological fluid in a flow path;

splitting the flow path into a first flow path and a second flow path;

propagating a first flow of said biological fluid in the first flow path toward a first analysis instrument adapted to measure a first property of said biological fluid;

propagating a second flow of said biological fluid in the second flow path toward a second analysis instrument, said second analysis instrument being adapted to analyze a volume of biological fluid containing platelets, small particles and/or microparticles contained in a chamber, said biological fluid at a controlled temperature;

without stopping said first flow, detecting when fluid is present in said chamber and then stopping said second flow, thereby obtaining stagnant fluid within said thermally controlled chamber;

adjusting a temperature of said stagnant fluid to a target temperature within said thermally controlled chamber; and measuring a property of said stagnant fluid using said second analysis instrument, thereby characterizing a second property of said biological sample.

16. The method of claim 15 wherein said second analysis instrument is defined by a dynamic light scattering (DLS) instrument and said step of stopping said second includes the step of stopping said second flow within an analysis chamber in said DLS instrument.

17. The method of claim 15 wherein the step of propagating a first flow comprises propagating said first flow of said biological fluid from a reservoir to one of a hematology analyzer and a flow cytometer.

18. The method of claim 17 further comprising measuring at least one of a presence, number and/or type of cellular elements in the biological fluid using the hematology analyzer or the flow cytometer.

* * * * *